(12) United States Patent
Yagyu

(10) Patent No.: US 12,128,150 B2
(45) Date of Patent: Oct. 29, 2024

(54) ULTRAVIOLET IRRADIATION DEVICE

(71) Applicant: Ushio Denki Kabushiki Kaisha, Tokyo (JP)

(72) Inventor: Hideaki Yagyu, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 406 days.

(21) Appl. No.: 17/764,078

(22) PCT Filed: Oct. 5, 2020

(86) PCT No.: PCT/JP2020/037737
§ 371 (c)(1),
(2) Date: Mar. 25, 2022

(87) PCT Pub. No.: WO2021/070780
PCT Pub. Date: Apr. 15, 2021

(65) Prior Publication Data
US 2022/0409755 A1 Dec. 29, 2022

(30) Foreign Application Priority Data
Oct. 7, 2019 (JP) .................. 2019-184792

(51) Int. Cl.
*A61L 2/10* (2006.01)
(52) U.S. Cl.
CPC .............. *A61L 2/10* (2013.01); *A61L 2202/11* (2013.01)
(58) Field of Classification Search
CPC .................. A61L 2/10; A61L 2202/11
See application file for complete search history.

(56) References Cited

U.S. PATENT DOCUMENTS 7,187,138 B2   3/2007  Kogure
10,910,210 B2  2/2021  Yagyu et al.
(Continued)

FOREIGN PATENT DOCUMENTS

JP   H09-171799 A   6/1997
JP   2003-036723 A  2/2003
(Continued)

OTHER PUBLICATIONS

Notification of Transmittal of Translation of the International Preliminary Report on Patentability (Chapter I) and Translation of Written Opinion of the International Searching Authority; PCT/JP2020/037737; mailed on Apr. 12, 2022.
(Continued)

*Primary Examiner* — Sean M Luck
(74) *Attorney, Agent, or Firm* — Kenichiro Yoshida

(57) ABSTRACT

Provided is a compact ultraviolet irradiation device in which a degree of an adverse effect on the human body is suppressed. The ultraviolet irradiation device includes: a lamp house on the surface of which a light extraction surface is formed; an excimer lamp accommodated in the lamp house, a main emission wavelength of which belongs to a first wavelength band of 190-225 nm; an optical filter that is arranged on the light extraction surface and substantially transmits the ultraviolet light in the first wavelength band and substantially reflect the ultraviolet light of a wavelength of 240-300 nm; and a reflecting surface that is a surface located outside the luminous tube of the excimer lamp and inclined with respect to the light extraction surface, the reflecting surface exhibiting reflectivity with respect to the ultraviolet light in the first wavelength band.

19 Claims, 11 Drawing Sheets

(56) References Cited

U.S. PATENT DOCUMENTS

| | | | | |
|---|---|---|---|---|
| 2007/0149086 A1* | 6/2007 | Nakamura | ............... | H01J 65/00 |
| | | | | 445/23 |
| 2015/0246148 A1* | 9/2015 | Blechschmidt | ........... | A61L 9/20 |
| | | | | 422/4 |
| 2019/0105415 A1* | 4/2019 | Gross | ........................ | A61L 2/10 |

FOREIGN PATENT DOCUMENTS

| | | | |
|---|---|---|---|
| JP | 2006-40867 A | 2/2006 | |
| JP | 2011-048968 A | 3/2011 | |
| JP | 6025756 B2 | 4/2014 | |
| JP | 2017-27912 A | 2/2017 | |
| JP | 2018-114197 A | 7/2018 | |
| JP | 2018-166091 A | 10/2018 | |
| WO | 2012122210 A1 | 9/2012 | |

OTHER PUBLICATIONS

Offfice Action of Jun. 29, 2023 for Corresponding Taiwanese Application 109134046, Citing JP 2017-27912A and Its English Summary of the Office Action.

* cited by examiner

ULTRAVIOLET IRRADIATION DEVICE

TECHNICAL FIELD

The present invention relates to an ultraviolet irradiation device.

BACKGROUND ART

It is conventionally known that DNA exhibits the highest absorption characteristic near a wavelength of 260 nm. A low-pressure mercury lamp shows a high emission spectrum near a wavelength of 254 nm. Therefore, conventionally, a technology of sterilizing by irradiating ultraviolet light from the low-pressure mercury lamp is widely used (refer to, for example, Patent Document 1).

However, light in the vicinity of the wavelength of 254 nm might adversely affect a human body when being irradiated to the human body. Following Patent Document 2 discloses a technology of performing sterilization while avoiding a risk to the human body by using ultraviolet light of a wavelength of 207-220 nm in a medical site.

PRIOR ART DOCUMENTS

Patent Documents

Patent Document 1: JP-A-2011-048968
Patent Document 2: Japanese Patent No. 6025756

SUMMARY OF THE INVENTION

Problems to be Solved by the Invention

However, Patent Document 2 mentioned above only refers that the ultraviolet light of the wavelength of 207-220 nm may be used for the sterilization in the medical site, and it is not assumed that general consumers generally perform the sterilization treatment in a non-medical site. For example, when the general consumers perform the sterilization in places in the home where bacteria are considered to be relatively easily grow such as toilet, kitchen, bathroom, and in shoes, conditions are imposed such as a size easy to carry and a minimal adverse effect on the human body.

However, at present, actually, no ultraviolet irradiation device suitable for sterilization applications that satisfies the above-described conditions has been proposed.

In view of the above-described problems, an object of the present invention is to provide a compact ultraviolet irradiation device in which a degree of an adverse effect on the human body is suppressed.

Means for Solving the Problems

An ultraviolet irradiation device according to the present invention is provided with:
a lamp house on at least one surface of which a light extraction surface is formed;
an excimer lamp accommodated in the lamp house in a position separated from the light extraction surface in a first direction, the excimer lamp that emits ultraviolet light, a main emission wavelength of which belongs to a first wavelength band of 190-225 nm;
a first electrode arranged in contact with an outer surface of a luminous tube of the excimer lamp;
a second electrode arranged in contact with the outer surface of the luminous tube of the excimer lamp in a position separated from the first electrode in a second direction parallel to a tube axis of the excimer lamp;
an optical filter that is arranged on the light extraction surface and substantially transmits the ultraviolet light in the first wavelength band but does not substantially transmit ultraviolet light of a wavelength of 240-300 nm; and
a reflecting surface that is a surface located outside the luminous tube of the excimer lamp and inclined with respect to the light extraction surface as seen in the second direction, the reflecting surface exhibiting reflectivity with respect to the ultraviolet light in the first wavelength band.

In this specification, the "main emission wavelength" indicates a wavelength $\lambda i$ in a wavelength range $Z(\lambda i)$ showing integrated intensity of 40% or larger with respect to the total integrated intensity in an emission spectrum in a case where a wavelength range $Z(\lambda)$ of ±10 nm with respect to a certain wavelength $\lambda$, is defined on the emission spectrum. For example, in a light source having an extremely narrow half-value width and showing light intensity only at a specific wavelength such as an excimer lamp in which a luminescent gas containing KrCl, KrBr, and ArF is sealed, a wavelength having the highest relative intensity (main peak wavelength) may be usually made the main emission wavelength.

In this specification, the description that the optical filter "substantially transmits the ultraviolet light" is intended to mean that intensity of the ultraviolet light transmitted through the optical filter is 60% or larger of the intensity of the ultraviolet light incident on the optical filter. In this specification, the description "not substantially transmit the ultraviolet light" is intended to mean that the intensity of the ultraviolet light transmitted through the optical filter is less than 20% of the intensity of the ultraviolet light incident on the optical filter.

Note that the optical filter may substantially reflect the ultraviolet light of the wavelength of 240-300 nm. Here, in this specification, the description "substantially reflects the ultraviolet light" is intended to mean that the intensity of the ultraviolet light reflected by the optical filter is 80% or more of the intensity of the ultraviolet light incident on the optical filter.

Transmittance and reflectance of the ultraviolet light of the optical filter actually change depending on an incident angle of the ultraviolet light incident on the optical filter. Note that, the incident angle is the angle between the normal of the incident surface of the optical filter and the ultraviolet light incident on the incident surface of the optical filter. Here, the ultraviolet light emitted from the excimer lamp travels with a certain divergence angle; among all the traveling light rays, intensity of the light ray traveling at an incident angle in the vicinity of 0° with respect to a light emission surface is the strongest, and the intensity decreases as the divergence angle is farther from 0°. Therefore, the optical filter having the transmittance of 60% or larger with respect to the intensity of the ultraviolet light incident on the optical filter at the incident angle of 20° or smaller may be treated as the filter that substantially transmits the ultraviolet light. Similarly, the optical filter exhibiting the transmittance of less than 20% with respect to the intensity of the ultraviolet light incident on the optical filter at the incident angle of 20° or smaller may be treated as the filter that does not substantially transmit the ultraviolet light. Similarly, the optical filter exhibiting the reflectance of 90% or larger with respect to the intensity of the ultraviolet light incident on the optical filter at the incident angle of 20° or smaller may be treated as the filter that substantially reflects the ultraviolet light.

The ultraviolet irradiation device is provided with the first electrode and the second electrode in contact with the outer surface of the luminous tube of the excimer lamp. These electrodes are in contact with the outer surface of the luminous tube of the excimer lamp in positions separated from each other in a tube axis direction of the excimer lamp. Therefore, the excimer lamp may discharge by a simple straight tube type structure, so that it is not necessary to adopt a structure in which double tube bodies are concentrically provided and a luminescent gas is sealed between an inner tube and an outer tube, a so called "double tube structure" generally used as a conventional excimer lamp.

As an example, a size of the luminous tube of the excimer lamp provided on the ultraviolet irradiation device is such that a length in the tube axis direction (second direction) is 15-200 mm, and an outer diameter is 2-16 mm.

In the excimer lamp that emits the ultraviolet light, the main emission wavelength of which belongs to the first wavelength band, also, ultraviolet light in a wavelength band (wavelength of 240-300 nm) that may affect the human body may be emitted although intensity thereof is extremely small. FIG. 1 is a view illustrating an example of an emission spectrum of the excimer lamp (main peak wavelength is in the vicinity of 222 nm) containing KrCl in the luminescent gas.

With reference to FIG. 1, a light output is observed also in the wavelength band of 240 nm or longer although this is very small. Note that not only the excimer lamp containing KrCl as the luminescent gas but also other excimer lamps that emit the ultraviolet light, the main emission wavelength of which belongs to the first wavelength band, such as the excimer lamp containing KrBr as the luminescent gas (main peak wavelength is 207 nm) and the excimer lamp containing ArF as the luminescent gas (main peak wavelength is 193 nm) may similarly emit the ultraviolet light of the wavelength of 240-300 nm.

As described above, in the ultraviolet irradiation device according to the present invention, the optical filter that substantially transmits the ultraviolet light in the first wavelength band and substantially reflects the ultraviolet light of the wavelength of 240-300 nm is arranged on a light extraction surface side. Therefore, components of a wavelength of 240-300 nm contained in the ultraviolet light emitted from the excimer lamp are substantially reflected by the optical filter, so that the amount of the light extracted out of the ultraviolet irradiation device decreases. That is, by providing such optical filter, an amount of light extracted to the outside further decreases (although they are originally the components of the wavelength band of a small light output), so that the effect on the human body is further suppressed.

By the way, as described above, transmittance and reflectance of the ultraviolet light of the optical filter change depending on the incident angle of the ultraviolet light incident on the optical filter. Even in the ultraviolet light of the first wavelength band, which are supposed to be extracted from the ultraviolet irradiation device, when the incident angle on the optical filter becomes extremely large, the transmittance decreases and the reflectance increases. Therefore, out of the ultraviolet light in the first wavelength band emitted from the excimer lamp, a part of the ultraviolet light incident on the optical filter at a relatively large incident angle (for example, 30° or larger) is reflected by the optical filter to be returned to the excimer lamp side. As a result, this is not extracted out of the ultraviolet irradiation device, and light extraction efficiency is lowered to a certain extent as compared with a case where the optical filter is not provided.

A part of the reflected light may be irradiated to a housing (casing) of the lamp house, and the lamp house may deteriorate.

In contrast, the ultraviolet irradiation device according to the present invention is provided with a reflecting surface exhibiting reflectivity with respect to ultraviolet light, the reflecting surface located outside a luminous tube and inclined with respect to the light extraction surface as seen in the second direction, that is, in the tube axis direction of the luminous tube of the excimer lamp. The ultraviolet light emitted from the excimer lamp travels toward the optical filter with a predetermined divergence angle. Here, when ultraviolet light traveling with a large divergence angle is incident on the reflecting surface, this is reflected by the reflecting surface to change the travel direction. Since the reflecting surface is formed of the surface inclined with respect to the light extraction surface, the incident angle at the time of incidence on the optical filter after reflection by the reflecting surface decreases.

As a result, a proportion of the ultraviolet light transmitted through the optical filter increases, an output of the ultraviolet light in the first wavelength band extracted from the ultraviolet irradiation device increases, and an effect of suppressing the degree of deterioration of the lamp house is obtained.

Note that, the description "the optical filter is arranged on the light extraction surface" includes a case where the optical filter is arranged in a position separated from the light extraction surface at a minute distance (for example, a few millimeters to dozen millimeters) in the first direction in addition to a case where the optical filter is arranged so as to be completely integral with the light extraction surface.

The first electrode may be a first electrode block in the shape of a block and a the second electrode may be a second electrode block in the shape of a block, and at least one of the first electrode block and the second electrode block may include a tapered surface forming the reflecting surface in a position away from the excimer lamp in a third direction orthogonal to the first direction and the second direction.

That is, the tapered surface forming the reflecting surface may be a part of the first electrode block or the second electrode block. In this case, both the first electrode block and the second electrode block are preferably made of a material exhibiting reflectivity with respect to the ultraviolet light in the first wavelength band (Al, Al alloy, stainless steel and the like). Furthermore, it is more preferable that both the first electrode block and the second electrode block include the tapered surface.

According to such a configuration, since the ultraviolet light in the first wavelength band traveling from the excimer lamp with a large divergence angle is reflected by both the electrode blocks, an amount of light with a reduced incident angle on the optical filter increases. As a result, the light extraction efficiency may be further improved, and the effect of suppressing the degree of deterioration of the lamp house is enhanced.

The ultraviolet irradiation device may be provided with the plurality of excimer lamps arranged separated from each other in the third direction, in which the first electrode block and the second electrode block may be arranged so as to straddle the plurality of excimer lamps while being in contact with the outer surface of the luminous tube of each of the plurality of excimer lamps, and the tapered surface may be at least formed in a position interposed between the plurality of excimer lamps adjacent to each other in the third direction as seen in the second direction.

A part of the tapered surface may be located closer to the light extraction surface than the excimer lamp in the first direction. According to such configuration, it is possible to reflect the ultraviolet light that would have been incident on the optical filter at an incident angle with a low proportion of transmission (transmittance) through the optical filter if there is no tapered surface, thereby further improving the amount of light that may be incident on the optical filter at an incident angle with a high proportion of transmission through the optical filter.

The tapered surface preferably has an angle of 10°-50° and more preferably has an angle of 20°-40° from the first direction as seen in the second direction.

Effect of the Invention

According to the present invention, a compact ultraviolet irradiation device in which the degree of the adverse effect on the human body is suppressed is achieved.

MODE FOR CARRYING OUT THE INVENTION

Figure 1:
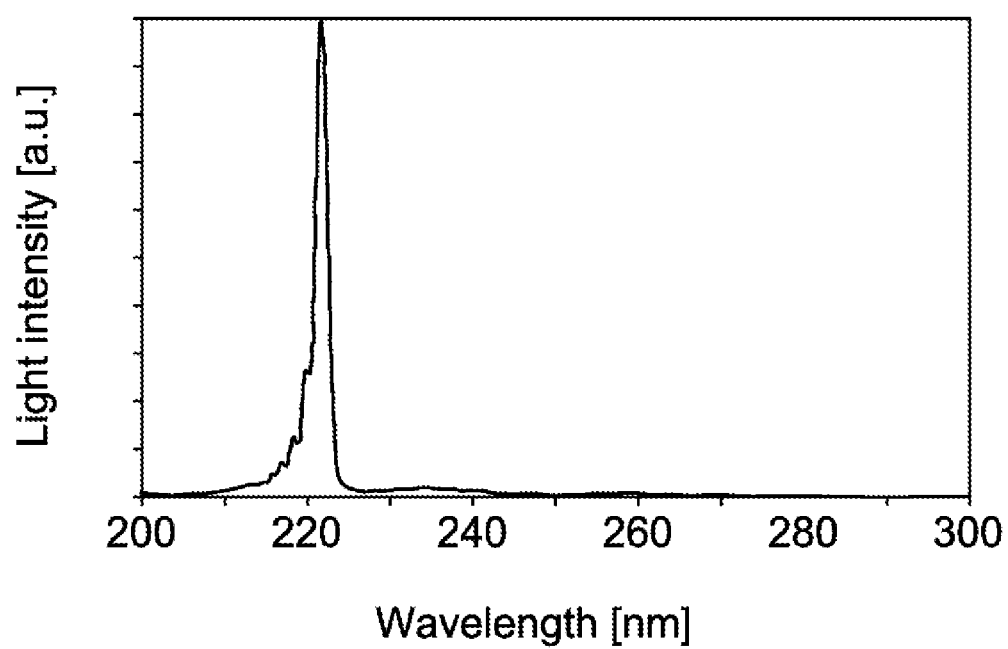
FIG. 1 is an example of an emission spectrum of an excimer lamp in which a luminescent gas contains KrCl.

An embodiment of an ultraviolet irradiation device according to the present invention is described with reference to the drawings as appropriate. Note that the following drawings are schematically illustrated, and a dimensional ratio on the drawing and an actual dimensional ratio do not always match. Furthermore, the dimensional ratios do not always the same between the drawings.

Figure 2:
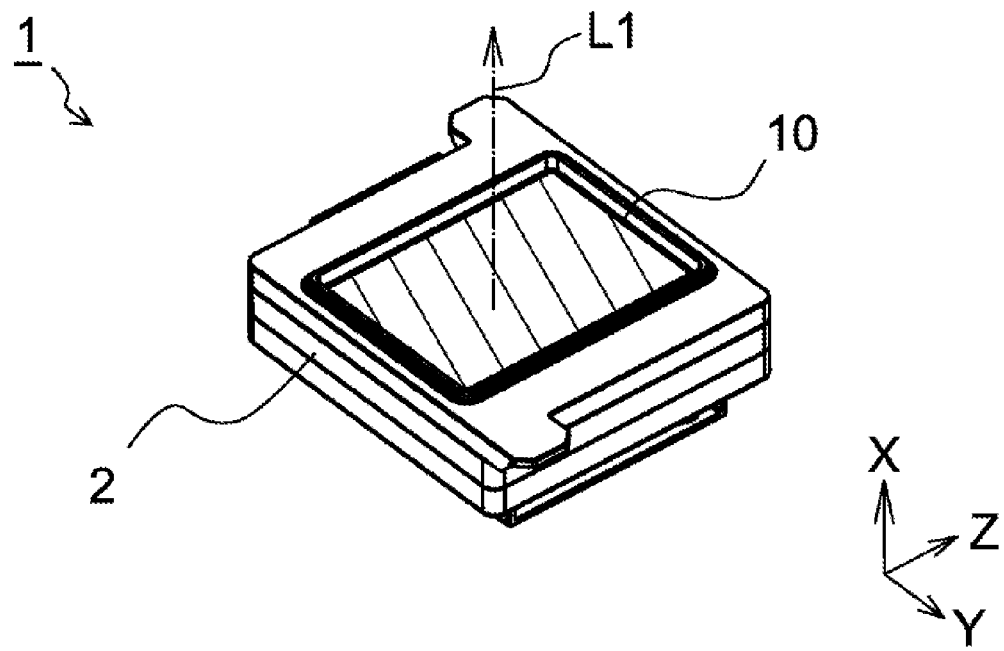
FIG. 2 is a perspective view schematically illustrating an appearance of an ultraviolet irradiation device.
Figure 3:
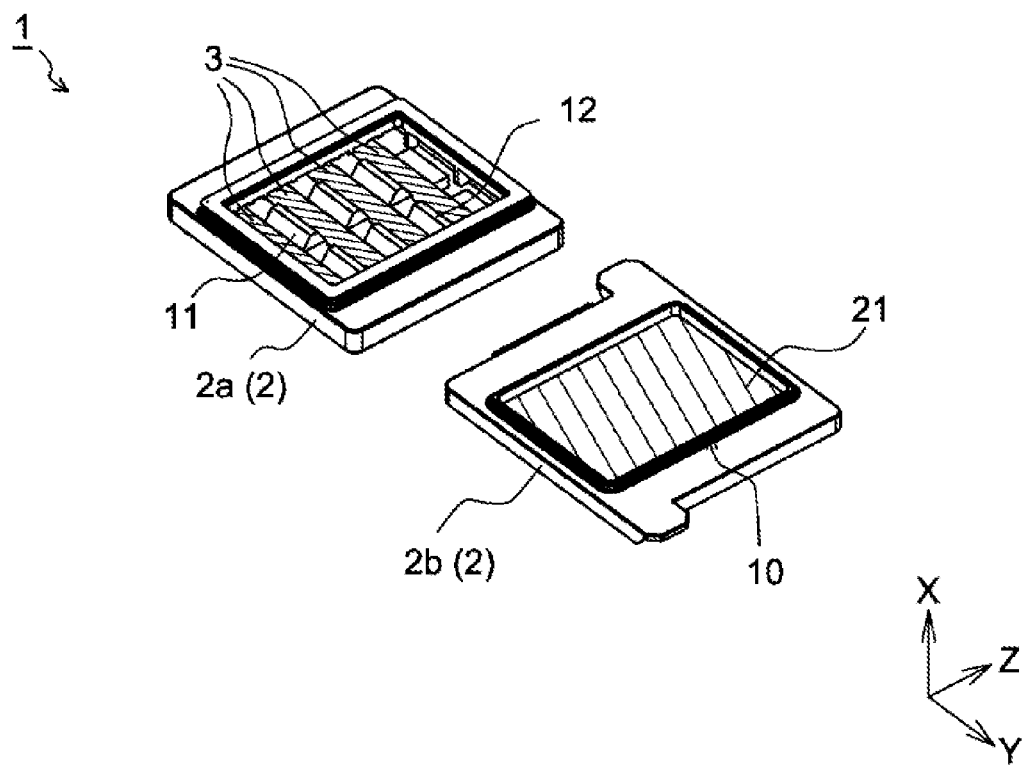
FIG. 3 is an exploded perspective view of a main body casing and a lid of a lamp house of the ultraviolet irradiation device in FIG. 2.

FIG. 2 is a perspective view schematically illustrating an appearance of the ultraviolet irradiation device. FIG. 3 is an exploded perspective view of a main body casing 2a and a lid 2b of a lamp house 2 of the ultraviolet irradiation device 1 in FIG. 2.

In each of following drawings, it is illustrated with reference to an X-Y-Z coordinate system in which an extraction direction of ultraviolet light L1 is an X direction, and a plane orthogonal to the X direction is a YZ plane. In further detail, as described later with reference to FIG. 3 and subsequent drawings, a tube axis direction of an excimer lamp 3 is a Y direction, and a direction orthogonal to the X direction and the Y direction is a Z direction. The X direction corresponds to a "first direction", the Y direction corresponds to a "second direction", and the Z direction corresponds to a "third direction".

In the following description, in a case where positive and negative directions are distinguished from each other when expressing the direction, they are represented with positive and negative signs such as a "+X direction" and a "−X direction". In a case of expressing the direction without distinguishing between positive and negative directions, this is simply represented as the "X direction". That is, in this specification, in a case where it is simply represented as the "X direction", both the "+X direction" and "−X direction" are included. The same applies to the Y direction and the Z direction.

As illustrated in FIGS. 2 and 3, the ultraviolet irradiation device 1 is provided with the lamp house 2 on one surface of which a light extraction surface 10 is formed. The lamp house 2 is provided with the main body casing 2a and the lid 2b, and the excimer lamp 3 and electrode blocks (11, 12) are accommodated in the main body casing 2a. Note that, although a case where four excimer lamps 3 (3a, 3b, 3c, 3d) are accommodated in the lamp house 2 is described as an example in this embodiment (refer to FIG. 4), the number of excimer lamps 3 may be one, two, three, or five or more. The electrode blocks (11, 12) form electrodes for supplying power to each excimer lamp 3.

In this embodiment, as illustrated in FIG. 3, an optical filter 21 is provided in an area forming the light extraction surface 10 of the lid 2b. A characteristic of the optical filter 21 is described later.

Figure 4:
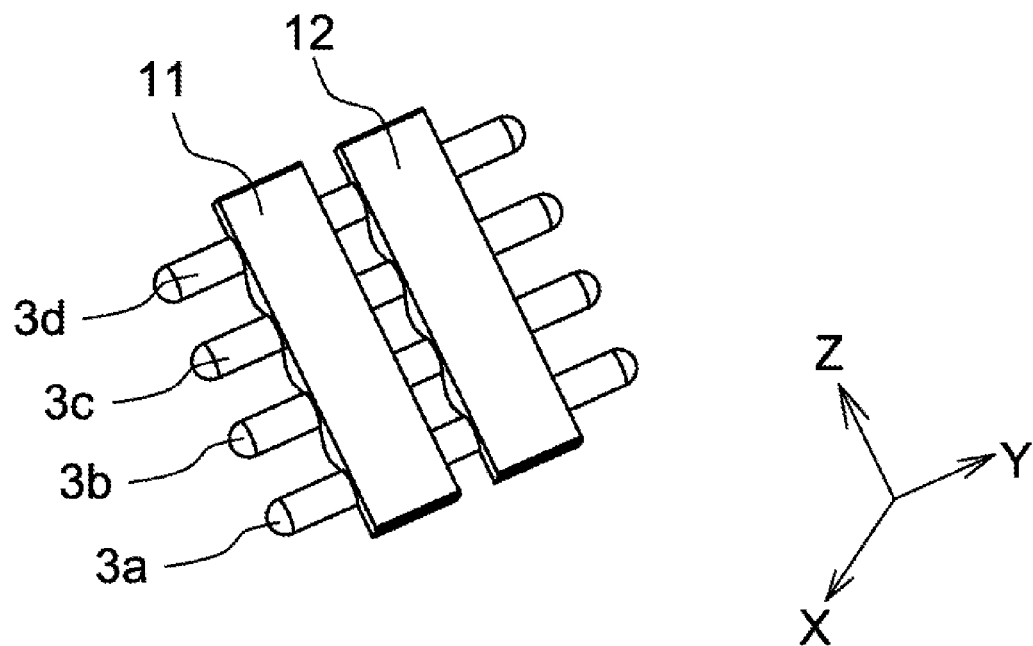
FIG. 4 is a perspective view schematically illustrating a structure of an electrode block and an excimer lamp provided on the ultraviolet irradiation device.
Figure 5:
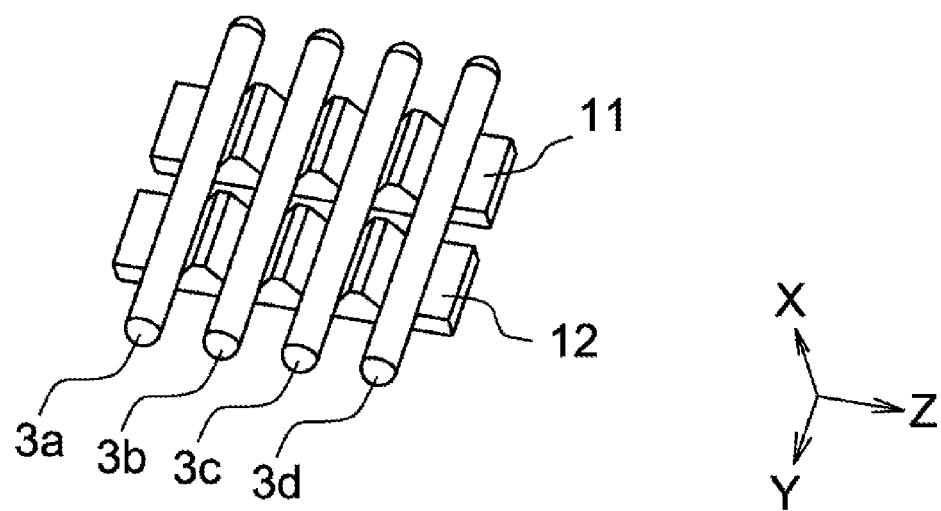
FIG. 5 is a perspective view from a different viewing point from FIG. 4.

FIGS. 4 and 5 are perspective views obtained by omitting the main body casing 2a from FIG. 3 and illustrating only the electrode blocks (11, 12) and the excimer lamps 3 (3a, 3b, 3c, 3d). Only a viewing angle is different between FIGS.

Figure 6:
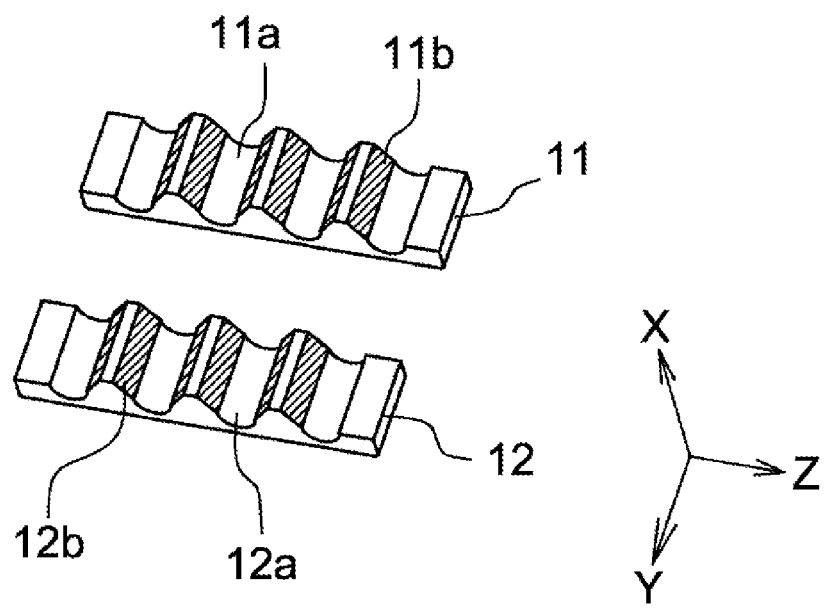
FIG. 6 is a perspective view schematically illustrating the structure of the electrode block while omitting the excimer lamp from FIG. 5.

4 and 5. FIG. 6 is a perspective view obtained by further omitting the excimer lamp 3 from FIG. 5.

As illustrated in FIGS. 4 and 5, the ultraviolet irradiation device 1 of this embodiment is provided with the four excimer lamps 3 (3a, 3b, 3c, 3d) arranged so as to be separated from each other in the Z direction. The two electrode blocks (11, 12) are arranged so as to be in contact with an outer surface of a luminous tube of each excimer lamp 3. Hereinafter, the electrode block 11 is referred to as a "first electrode block 11" and the electrode block 12 is referred to as a "second electrode block 12" as appropriate. Note that the first electrode block 11 corresponds to a "first electrode", and the second electrode block 12 corresponds to a "second electrode".

The first electrode block 11 and the second electrode block 12 are arranged in positions separated from each other in the Y direction. As illustrated in FIG. 6, the first electrode block 11 includes a mounting area 11a having a shape along a curved surface of the outer surface of the luminous tube of the excimer lamp 3 on which the excimer lamp 3 is mounted, and a tapered surface 11b formed in a position away from the excimer lamp 3 in the Z direction inclined with respect to the YZ plane. Similarly, the second electrode block 12 also includes a mounting area 12a and a tapered surface 12b.

Note that the first electrode block 11 and the second electrode block 12 are made of conductive materials, preferably materials exhibiting reflectivity with respect to the ultraviolet light L1 in a first wavelength band. As an example, both the first electrode block 11 and the second electrode block 12 are formed of Al, Al alloy, stainless steel and the like.

Figure 7:
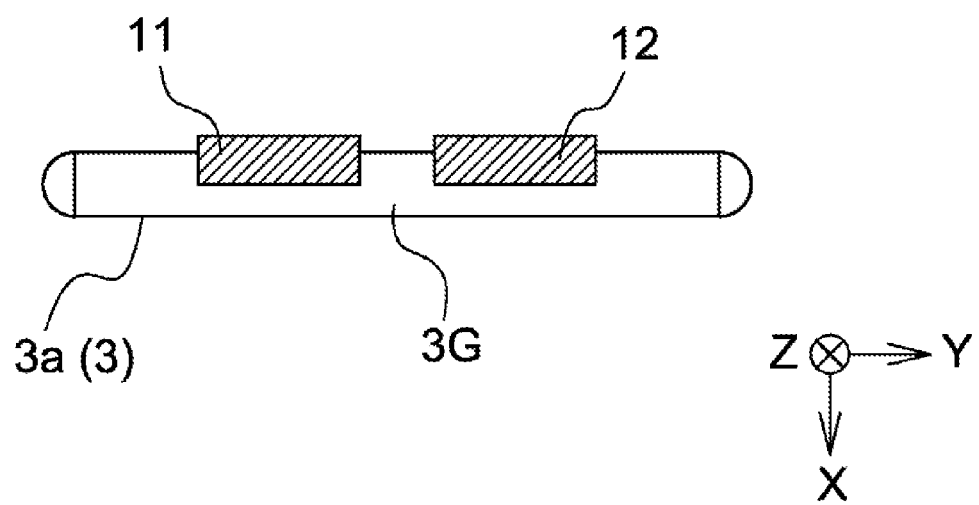
FIG. 7 is a schematic plan view of the excimer lamp as seen in a Z direction.

FIG. 7 is a view schematically illustrating a positional relationship between the excimer lamp 3 and the electrode blocks (11, 12), the view corresponding to a schematic plan view of the excimer lamp 3 as seen in a +Z direction. Note that, in FIG. 7, out of the four excimer lamps 3 (3a, 3b, 3c, 3d), only the excimer lamp 3a located closest to a −Z side is illustrated, and the other excimer lamps (3b, 3c, 3d) are not illustrated; however, the excimer lamps (3b, 3c, 3d) are also arranged in the +Z direction as described above.

The excimer lamp 3 includes the luminous tube a tube axis direction of which is the Y direction, and the outer surface of the luminous tube of the excimer lamp 3 is in contact with each of the electrode blocks (11, 12) in positions separated from each other in the Y direction. A luminescent gas 3G is sealed in the luminous tube of the excimer lamp 3. When a high-frequency AC voltage of, for example, about 10 kHz to 5 MHz is applied between the electrode blocks (11, 12), the voltage is applied to the luminescent gas 3G via the luminous tube of the excimer lamp 3. At that time, discharge plasma is generated in a discharge space in which the luminescent gas 3G is sealed, an atom of the luminescent gas 3G is excited to enter an excimer state, and excimer light emission is generated when this atom shifts to a ground state.

The luminescent gas 3G is made of a material that emits the ultraviolet light L1, a main emission wavelength of which belongs to the first wavelength band of 190-225 nm at the time of excimer light emission. As an example, the luminescent gas 3G contains KrCl, KrBr, and ArF. Note that, in addition to the above-described gas types, an inert gas such as argon (Ar) or neon (Ne) may also be mixed.

For example, in a case where the luminescent gas 3G contains KrCl, the excimer lamp 3 emits the ultraviolet light L1 the main peak wavelength of which is in the vicinity of 222 nm. In a case where the luminescent gas 3G contains KrBr, the excimer lamp 3 emits the ultraviolet light the main peak wavelength of which is in the vicinity of 207 nm. In a case where the luminescent gas 3G contains ArF, the excimer lamp 3 emits the ultraviolet light L1 the main peak wavelength of which is in the vicinity of 193 nm. A spectrum of the ultraviolet light L1 emitted from the excimer lamp 3 in which the luminescent gas 3G contains KrCl is as described above with reference to FIG. 1.

As illustrated in FIG. 1, in a case where the luminescent gas 3G contains KrCl, in the spectrum of the ultraviolet light L1, a light output is concentrated in the vicinity of 222 nm being substantially the main peak wavelength, but also in the wavelength band of 240 nm or longer, which might affect a human body, a light output is observed although this is very small. Therefore, the optical filter 21 is provided in the area forming the light extraction surface 10 for the purpose of blocking light components in such wavelength band.

Figure 8:
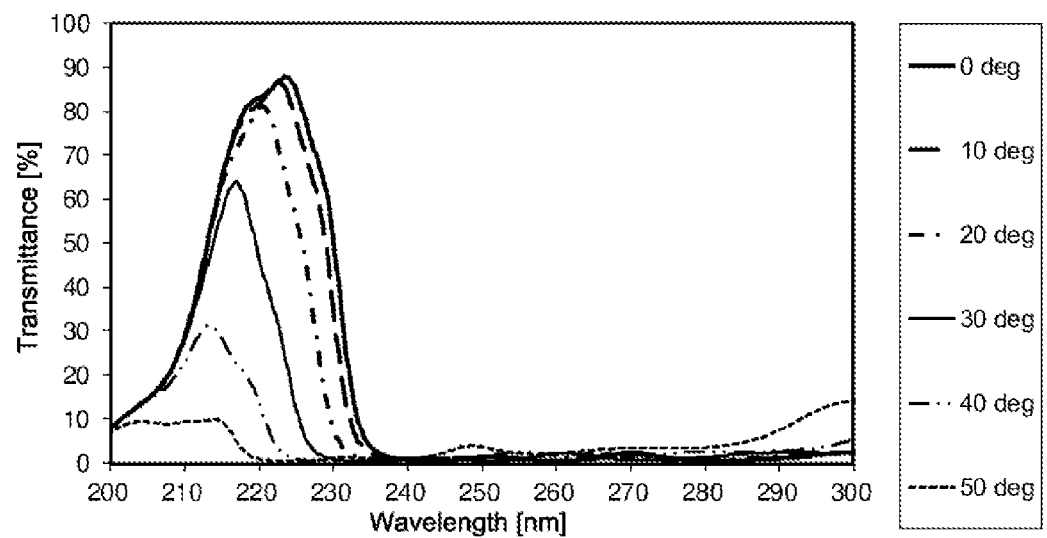
FIG. 8 is a graph illustrating an example of a transmission spectrum of an optical filter.
Figure 9:
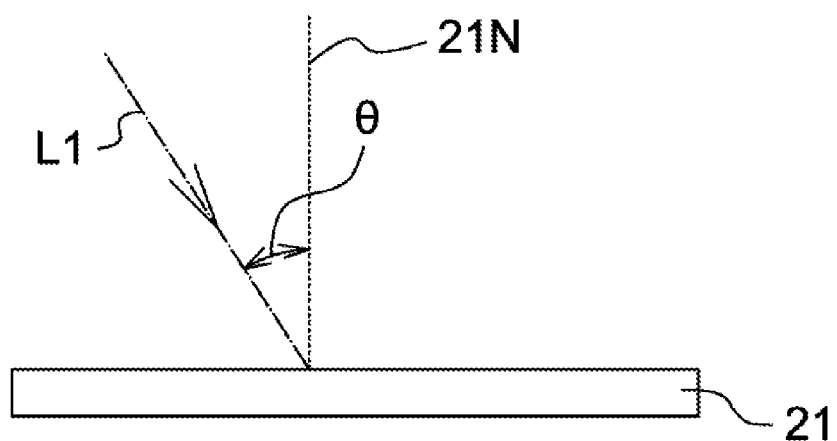
FIG. 9 is a schematic diagram for illustrating an incident angle of ultraviolet light on the optical filter.

FIG. 8 is a graph illustrating an example of a transmission spectrum of the optical filter 21 obtained by measuring a ratio of intensity of light emitted from the optical filter 21 to intensity of light incident on the optical filter 21 for each wavelength. Note that, in FIG. 8, the transmission spectrum is illustrated for each incident angle θ when the ultraviolet light L1 is incident on the optical filter 21. Here, the incident angle θ is defined by an angle between a normal line 21N with respect to an incident surface of the optical filter 21 and the ultraviolet light L1 incident on the incident surface of the optical filter 21 as illustrated in FIG. 9.

The optical filter 21 having a characteristic illustrated in FIG. 8 is designed assuming a case where the luminescent gas 3G of the excimer lamp 3 contains KrCl, that is, a case where the excimer lamp 3 emits the ultraviolet light L1 the main peak wavelength of which is 222 nm. That is, as illustrated in FIG. 8, this optical filter 21 substantially transmits the ultraviolet light L1 in the vicinity of the wavelength of 222 nm, more specifically in the wavelength band of 218-226 nm, but does not substantially transmit the ultraviolet light L1 of 240-300 nm. The optical filter 21 may be designed to substantially transmit the ultraviolet light L1 of wavelength components in the vicinity of the main peak wavelength out of the ultraviolet light L1 emitted from the excimer lamp 3, but not to substantially transmit the ultraviolet light L1 of 240-300 nm.

According to the optical filter 21 illustrated in FIG. 8, the ultraviolet light L1 of 240-300 nm shows transmittance of 5% or less in a range of the incident angle θ of 0°-40°, and shows transmittance of 10% or less even in a case where the incident angle θ is 50°.

As described above, the optical filter 21 showing different transmittance depending on the wavelength of the incident ultraviolet light L1 is realized by a multilayer film composed of a plurality of materials having different refractive indices. In contrast, in a case where the optical filter 21 is formed of the plurality of dielectric multilayer films having different refractive indices, the transmittance inevitably changes depending on the incident angle θ of the ultraviolet light L1 with respect to the optical filter 21. As a result, as illustrated in FIG. 8, the transmittance of the components in the vicinity of the main peak wavelength (222 nm, in this example) also decreases depending on the incident angle θ of the ultraviolet light L1 with respect to the optical filter 21. For example, with reference to FIG. 8, in a case where the incident angle θ is 40° or larger, the transmittance with respect to the ultraviolet light L1 in the vicinity of 222 nm is less than 20%.

Figure 10:
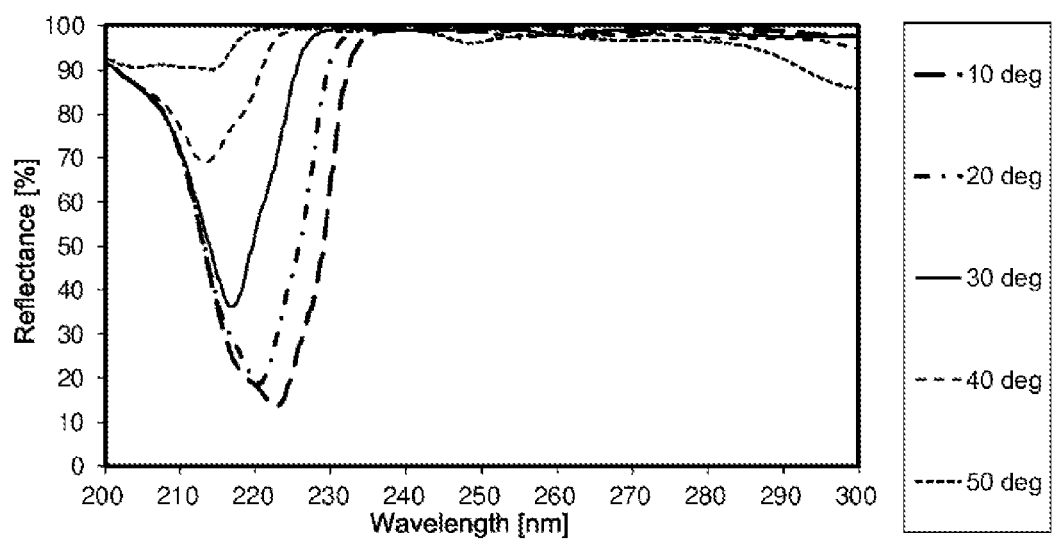
FIG. 10 is a graph illustrating an example of a reflection spectrum of the optical filter.

Note that, out of the ultraviolet light L1, a part of the ultraviolet light L1 not transmitted through the optical filter 21 is reflected by the optical filter 21. FIG. 10 is a graph illustrating an example of a reflection spectrum of the optical filter 21 obtained by measuring a ratio of intensity of light reflected by the optical filter 21 to the intensity of the light incident on the optical filter 21 for each wavelength. However, since a light emission unit and a light reception unit cannot be arranged on the same optical axis, data in a case where the incident angle θ is 0° is not illustrated in the graph in FIG. 10.

According to the optical filter 21 illustrated in FIG. 10, the ultraviolet light L1 of 240-300 nm shows reflectance of 95% or more in a range of the incident angle θ of 10°-40°, and shows reflectance of 90% or more even in a case where the incident angle θ is 50°.

Figure 11:
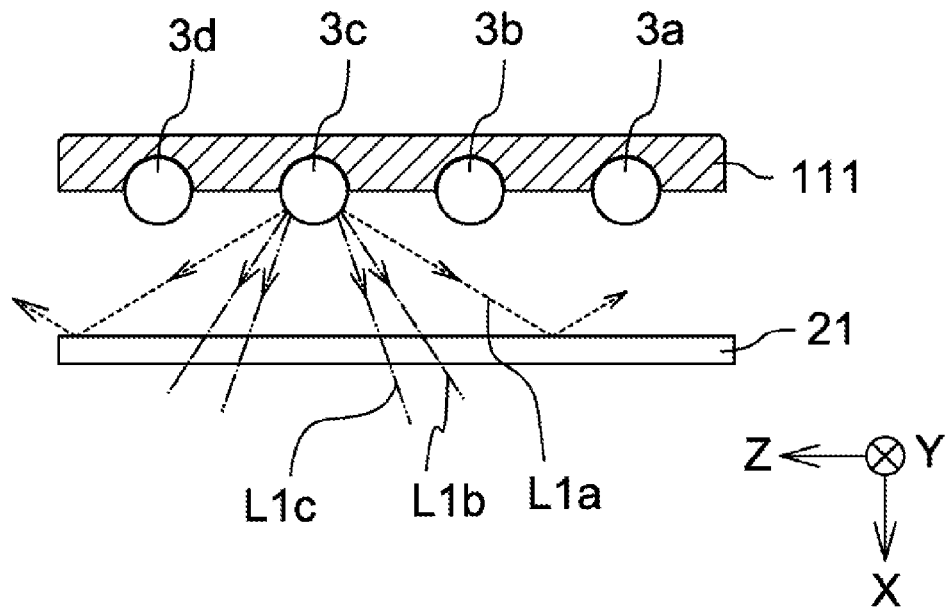
FIG. 11 is a view schematically illustrating a state of travel of ultraviolet light in a case where the ultraviolet irradiation device is provided with a first electrode block on which no tapered surface is formed.

Next, an effect of including the tapered surfaces (11b, 12b) of the electrode blocks (11, 12), respectively is described with reference to the drawings. FIG. 11 is a view schematically illustrating a state of travel of the ultraviolet light L1 emitted from the excimer lamp 3 toward the optical filter 21 in a case where a first electrode block 111 with no tapered surface formed is provided in place of the first electrode block 11. In FIG. 11, out of the ultraviolet light L1 emitted from each of the excimer lamps 3, the ultraviolet light L1 emitted from the excimer lamp 3c is representatively illustrated.

The ultraviolet light L1 emitted from each excimer lamp 3 travels toward the optical filter 21 with a predetermined divergence angle. Therefore, out of the ultraviolet light L1, as for ultraviolet lights (L1b, L1c) having a relatively small incident angle with respect to the optical filter 21, components in the vicinity of the main peak wavelength are substantially transmitted through the optical filter 21. However, as for ultraviolet light L1a having a relatively large incident angle with respect to the optical filter 21, a certain proportion of the ultraviolet light L1a is reflected by the optical filter 21 even in a case of the components in the vicinity of the main peak wavelength. Therefore, a phenomenon occurs that out of the ultraviolet light L1 emitted from each excimer lamp 3, a part of the components in the vicinity of the main peak wavelength being the wavelength band that is expected to be extracted cannot be extracted to the outside.

Figure 12:
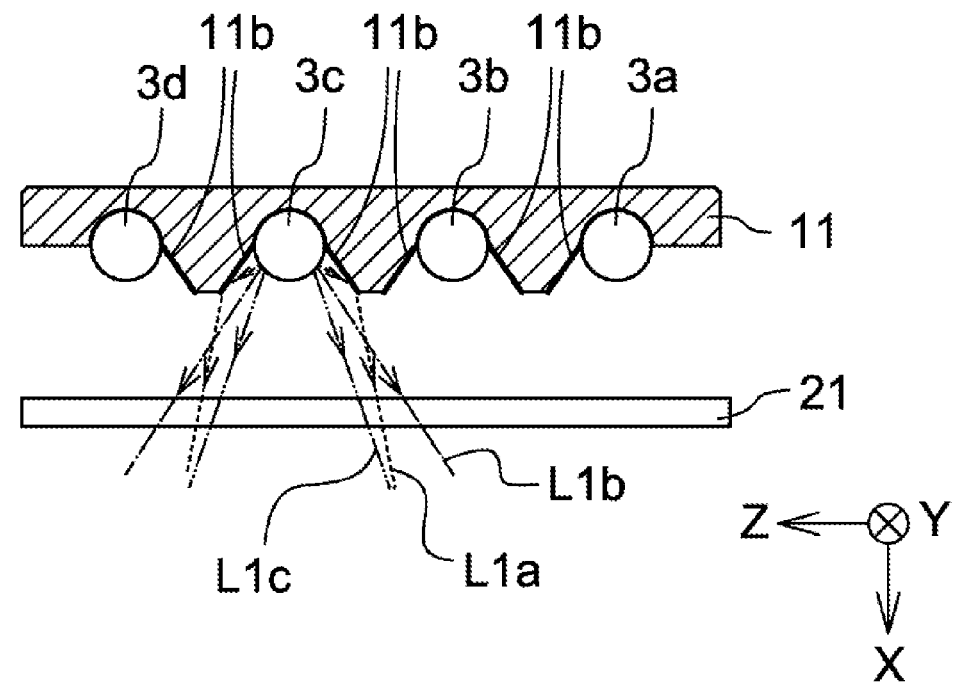
FIG. 12 is a view schematically illustrating a state of travel of ultraviolet light in a case where the ultraviolet irradiation device is provided with a first electrode block on which a tapered surface is formed.

In contrast, as in this embodiment, since the first electrode block 11 is provided with the tapered surface 11b, as illustrated in FIG. 12, the ultraviolet light L1a that travels with a relatively large divergence angle is reflected by the tapered surface 11b to change a travel direction. As a result, the incident angle when the ultraviolet light L1a is incident on the optical filter 21 becomes smaller than that in a case in FIG. 11, and an amount of light transmitted through the optical filter 21 increases. As a result, an amount of the ultraviolet light L1 in the vicinity of the main peak wavelength, which is emitted from each excimer lamp 3 and is extracted out of the ultraviolet irradiation device 1 is increased. On the contrary, an amount of return light reflected by the optical filter 21 to travel toward the excimer lamp 3 decreases, and progress in deterioration of the lamp house 2 is suppressed.

Note that, although the first electrode block 11 is described as an example in FIG. 12, for the similar reason, as for the second electrode block 12, an amount of light that may be extracted out of the ultraviolet irradiation device 1 of the ultraviolet light L1 in the vicinity of the main peak wavelength is improved by including the tapered surface 12b. That is, the tapered surfaces (11b, 12b) corresponds to "reflecting surface".

Example

An effect of taper angles of tapered surfaces (11a, 11b) of electrode blocks (11, 12), respectively, on illuminance of ultraviolet light L1 extracted from an ultraviolet irradiation device 1 was examined.

(Common Condition)

Four excimer lamps 3 were prepared in which a mixed gas of Kr, $Cl_2$, Ar, and Ne was sealed as a luminescent gas 3G in a tube body having a length of 70 mm in a tube axis direction (Y direction) and an outer diameter of φ6 mm. Then, these four excimer lamps 3 were brought into contact with the electrode blocks (11, 12) made of Al arranged so as to be separated from each other by 7 mm in the Y direction. Note that a separation distance between the excimer lamps 3 in a Z direction was set to 14 mm.

Under the above-described conditions, an AC voltage of a peak-to-peak value of about 4 kV and a frequency of 70 kHz was applied between the electrode blocks (11, 12) to generate dielectric barrier discharge for each excimer lamp 3, and illuminance in the center position of the four excimer lamps 3 away from a light extraction surface 10 by 20 mm in a +X direction was measured with an illuminometer. Note that an optical filter 21 having a transmission spectrum illustrated in FIG. 8 was installed on the light extraction surface 10.

Figure 13:
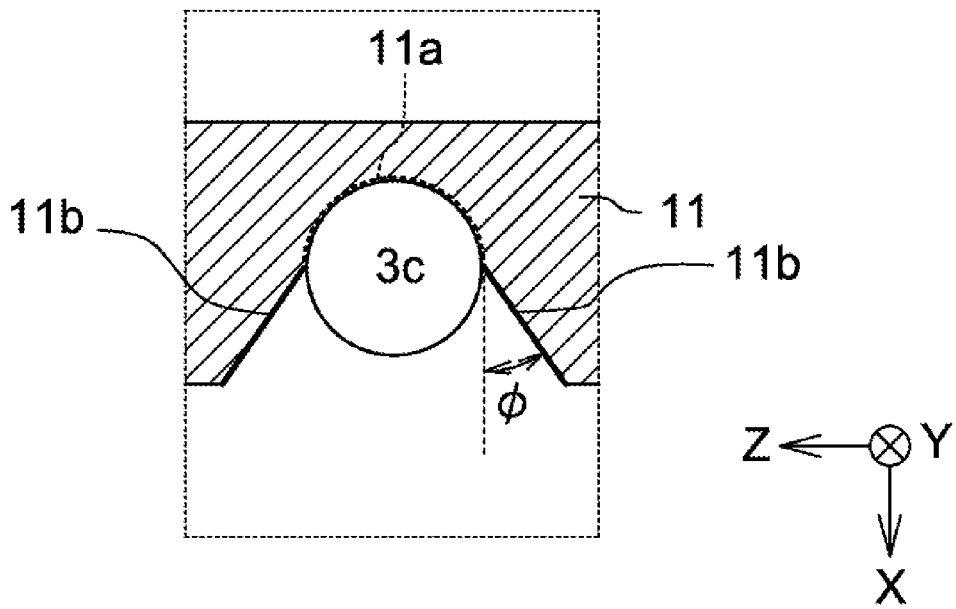
FIG. 13 is a schematic diagram for illustrating a taper angle.

As the electrode blocks (11, 12), a plurality of types having different taper angles φ illustrated in FIG. 13 were prepared, and the illuminance was measured similarly by using each of the electrode blocks (11, 12). Note that, when the taper angle φ was made different, the separation distance between the excimer lamps 3 was kept constant at 7 mm by adjusting a protruding distance of the tapered surfaces (11b, 12b) with respect to the excimer lamp 3 in an X direction.

Note that, for comparison, illuminance of a case where the electrode blocks having a taper angle φ of 0°, that is, the electrode blocks not provided with the tapered surfaces (11b, 12b) as is the case with an electrode block 111 illustrated in FIG. 11 are arranged in place of the electrode blocks (11, 12) was measured by a similar method.

Figure 14:
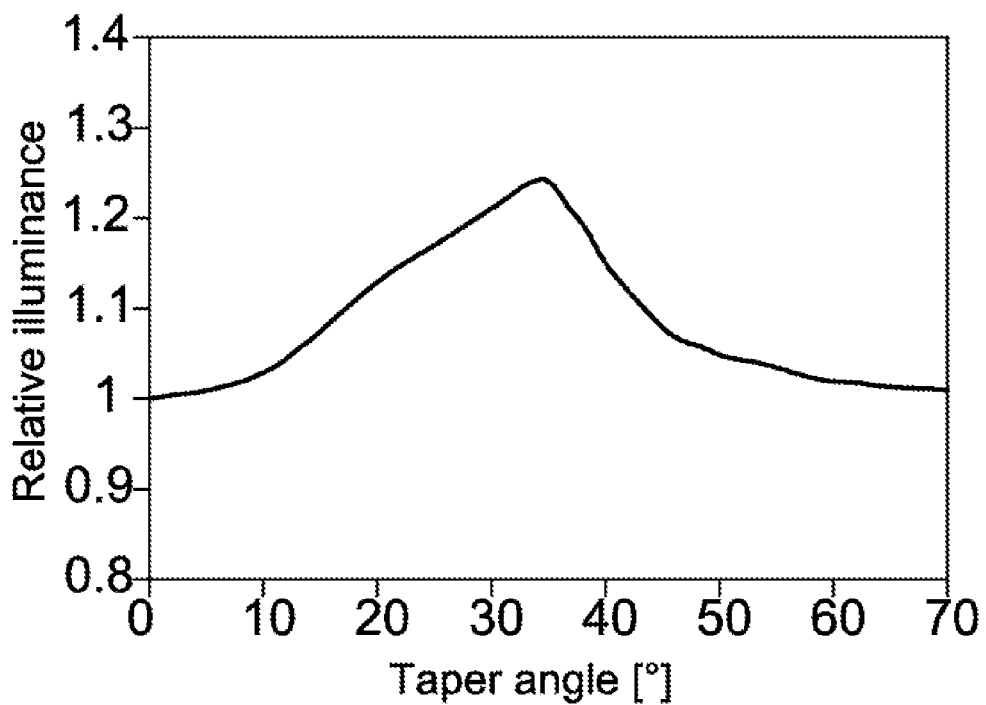
FIG. 14 is a graph illustrating a relationship between a taper angle φ of the tapered surface provided on the electrode block and illuminance of ultraviolet light extracted from the ultraviolet irradiation device.

The results are illustrated in Table 1 and FIG. 14. Note that, in Table 1 and FIG. 14, a value of relative illuminance with respect to the illuminance in a case of using the electrode blocks not provided with the tapered surfaces (11b, 12b) is illustrated for each taper angle φ. The taper angle φ is an inclination angle of the tapered surface (11b, 12b) with respect to an XY plane, and in Table 1 and FIG. 14, a case of inclining counterclockwise (positive taper angle) and a case of inclining clockwise (negative taper angle) are made the same value.

TABLE 1

| ANGLE (°) | ULTRAVIOLET RADIATION INTENSITY (a.u.) |
|---|---|
| 0 | 1 |
| 10 | 1.03 |
| 20 | 1.13 |
| 25 | 1.17 |
| 30 | 1.21 |
| 35 | 1.24 |
| 40 | 1.15 |
| 45 | 1.08 |
| 50 | 1.05 |
| 60 | 1.02 |
| 70 | 1.01 |

According to Table 1 and FIG. 14, it is understood that higher illuminance is realized in a case when the electrode blocks (11, 12) provided with the tapered surfaces (11b, 12b), respectively, are used as compared with a case where the electrode blocks not provided with the tapered surfaces (11b, 12b) are used, irrespective of the taper angle φ in a case where the taper angle φ is 70° or smaller.

Especially, in a case where the taper angle φ is 10°-50°, illuminance increase of 3% or more is realized as compared with a case of using the electrode blocks not provided with the tapered surfaces (11b, 12b). Furthermore, in a case where the taper angle φ is 20°-40°, illuminance of 10% or more is realized as compared with a case where the electrode blocks not provided with the tapered surfaces (11b, 12b) are used.

Figure 15:
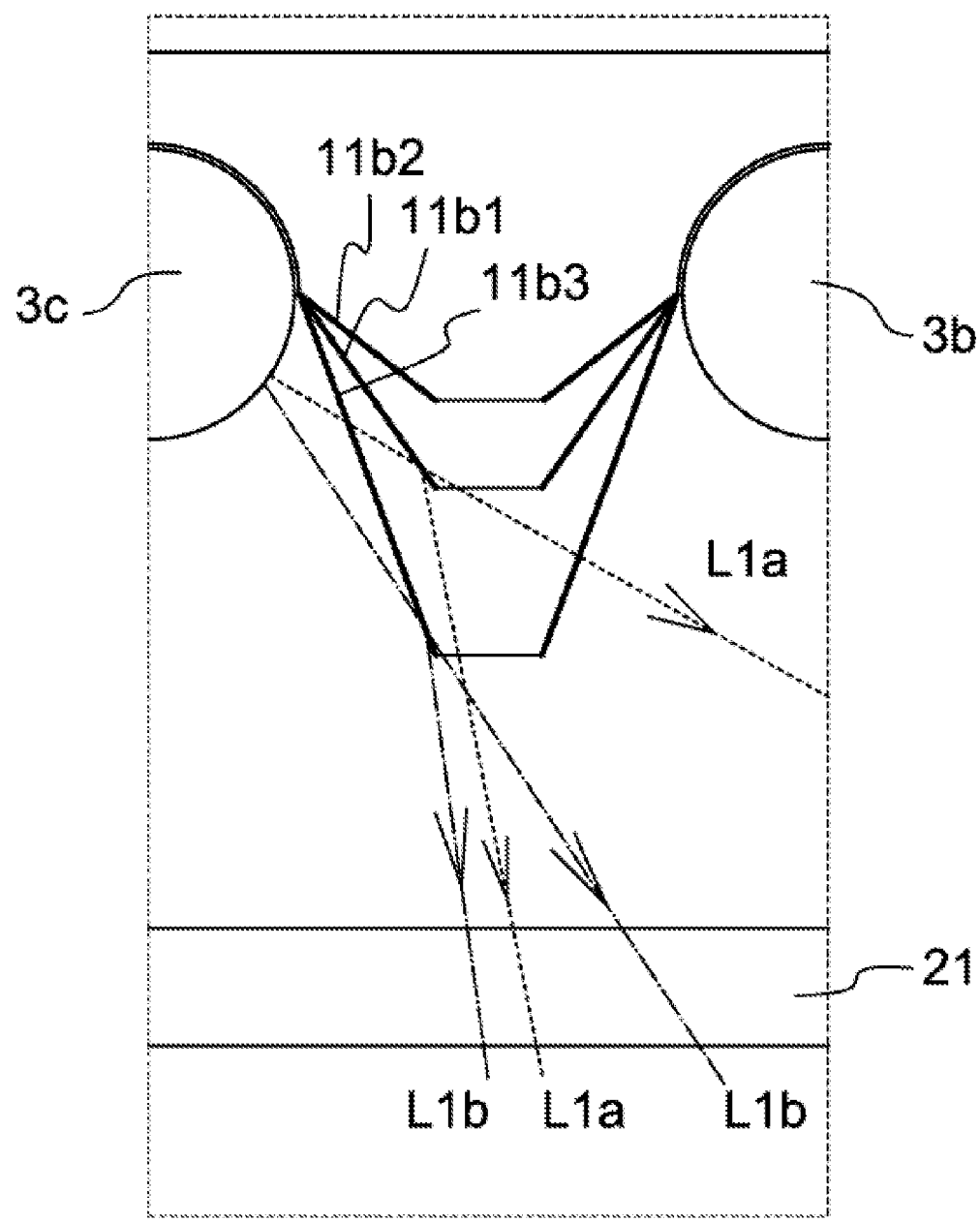
FIG. 15 is a schematic diagram for illustrating an effect of a value of the taper angle φ of the tapered surface on the ultraviolet light.

FIG. 15 is a schematic diagram for illustrating an effect of a size of the taper angle φ of the tapered surface 11b on the ultraviolet light L1; a tapered surface 11b1 having the taper angle φ of 20°-40°, a tapered surface 11b2 having the taper angle φ of 50° or larger, and a tapered surface 11b3 having the taper angle φ of 10° or smaller are all illustrated in the same drawing.

In a case where the taper angle φ of the tapered surface 11b is 50° or larger (tapered surface 11b2), out of the ultraviolet light L1 emitted from the excimer lamp 3, the ultraviolet light L1 reflected by the tapered surfaces (11b, 12b) to change the travel direction is limited to that with an extremely large divergence angle. That is, it is considered that, as a result of a fact that a component the incident angle θ of which is relatively large is still present (ultraviolet light L1a) out of the ultraviolet light L1 that travels straight without being incident on the tapered surfaces (11b, 12b) and is directly incident on the optical filter 21, the ultraviolet light L1a is not transmitted through the optical filter 21 and cannot be extracted, so that the illuminance is not sufficiently made high in a case where the taper angle φ of the tapered surface 11b is 50° or larger as compared with a case where the taper angle φ is smaller than 50°.

With reference to FIG. 15, if the first electrode block 11 includes the tapered surface 11b1, the ultraviolet light L1a is reflected by the tapered surface 11b1 to change the travel direction and is incident on the optical filter 21 at a relatively small incident angle θ. As a result, the ultraviolet light L1a is transmitted through the optical filter 21 to be extracted outside. In contrast, when the first electrode block 11 includes the tapered surface 11b2, the ultraviolet light L1a is not incident on the tapered surface 11b2, so that this travels straight, and as a result, this is incident on the optical filter 21 at a relatively large incident angle θ to be reflected by the optical filter 21 as described above.

In contrast, in a case where the taper angle φ of the tapered surface 11b is smaller than 10° (tapered surface 11b3), the ultraviolet light L1b that is incident on the optical filter 21 at a small incident angle such that this is transmitted through the optical filter 21 even when this travels straight without the tapered surface 11b3 might be incident on the tapered surface 11b3. With reference to FIG. 15, if the first electrode block 11 includes the tapered surface 11b1, the ultraviolet light L1b travels straight without being incident on the tapered surface 11b1 and is directly incident on the optical filter 21 at a relatively small incident angle θ. In contrast, if the first electrode block 11 includes the tapered surface 11b3, the ultraviolet light L1b is reflected by the tapered surface 11b3 to change the travel direction. Since this ultraviolet light L1b is incident on the optical filter 21 at a relatively small incident angle θ, this is taken out as it is, but as described above, as a result of reflecting the ultraviolet light L1 that originally does not have to be reflected by the tapered surface 11b1, a part of the ultraviolet light L1 is absorbed by the tapered surface 11b3, so that light extraction efficiency deteriorates as compared with a case where the tapered surface 11b1 is provided.

Another Embodiment

Hereinafter, another embodiment is described.

<1> In the above-described embodiment, a case where the first electrode block 11 includes both the tapered surface 11b inclined counterclockwise and the tapered surface 11b inclined clockwise with respect to the XY plane is described (refer to FIG. 13). However, the present invention does not exclude a case where the first electrode block 11 includes the tapered surface 11b that is inclined only either counterclockwise or clockwise with respect to the XY plane. The same applies to the second electrode block 12.

<2> In a case where the ultraviolet irradiation device 1 is provided with a plurality of excimer lamps 3, arrangement positions of the two or more excimer lamps 3 in the X direction may be displaced.

<3> In the above-described embodiment, it is described that the first electrode block 11 and the second electrode block 12 are arranged so as to be separated from each other in the Y direction. However, the first electrode block 11 and the second electrode block 12 may also be connected via an insulating member.

<4> In the above-described embodiment, it is described that the tapered surfaces (11b, 12b) are a part of the electrode blocks (11, 12), respectively. However, the tapered surfaces (11b, 12b) may also be formed of a reflecting member different from the forming material of the electrode blocks (11, 12) and exhibiting reflectivity with respect to the ultraviolet light L1 belonging to the first wavelength band.

<5> In the above-described embodiment, a case where a part of the tapered surface (11b, 12b) protrudes in the +X direction from the excimer lamp 3 is described. However, even in a case where an end in the +X direction of the tapered surfaces (11b, 12b) are located on the −X side as compared with an end on the +X end of the excimer lamp 3, the light extraction efficiency may be improved as compared with the electrode blocks not including the tapered surfaces (11b, 12b), respectively.

<6> In the above-described embodiment, a case where the tapered surfaces (11b, 12b) forming the reflecting surfaces are a part of the electrode blocks (11, 12) is described. However, as described above with reference to FIG. 12, as long as the reflecting surface has a function of reflecting the ultraviolet light L1a emitted from each excimer lamp 3 to travel with a relatively large divergence angle and making the incident angle when incident on the optical filter 21 small, this is not necessarily required to be a part of the electrode blocks (11, 12).

Figure 16A:
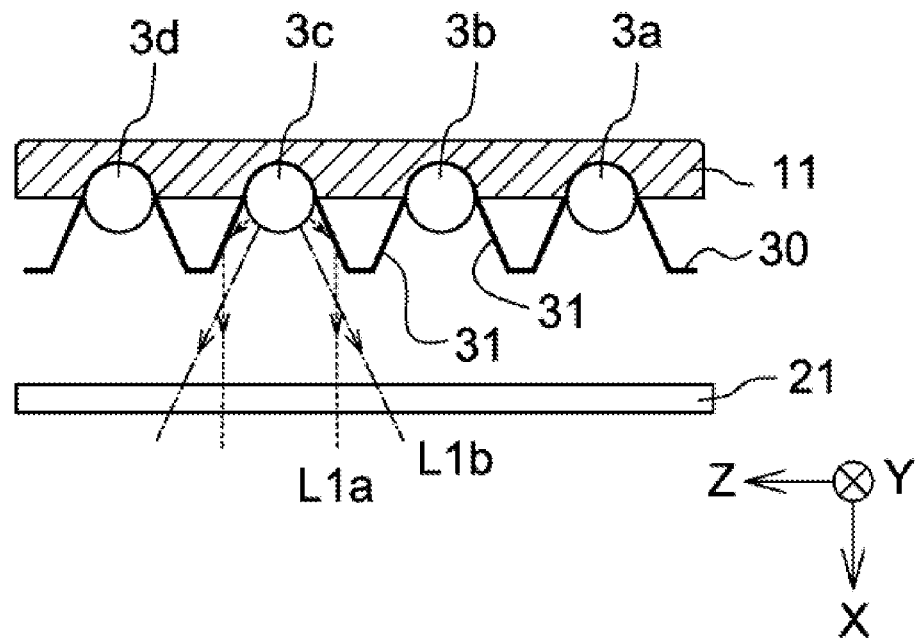
FIG. 16A is a view illustrating a schematic configuration of an ultraviolet irradiation device of another embodiment following FIG. 12.
Figure 16B:
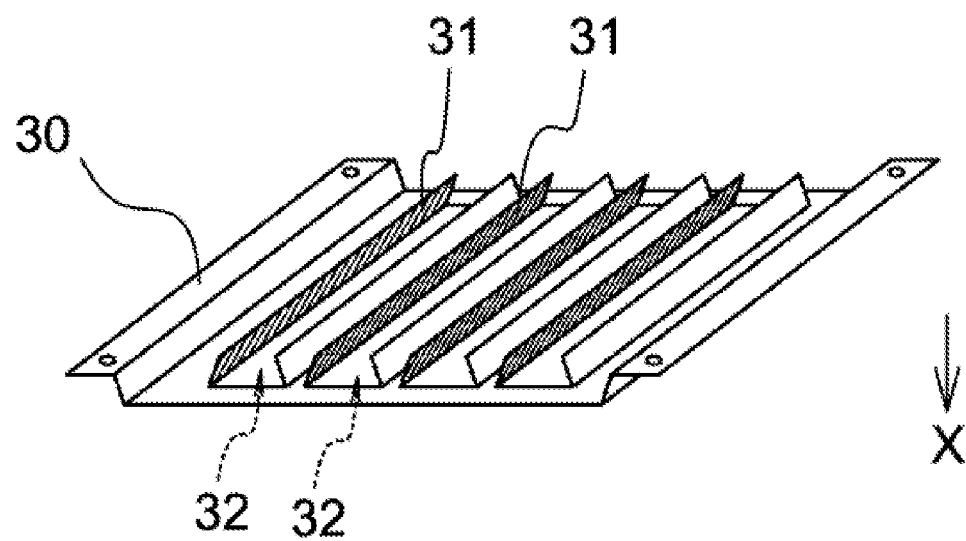
FIG. 16B is a perspective view schematically illustrating a structure of a reflecting member provided on the ultraviolet irradiation device illustrated in FIG. 16A.

For example, as illustrated in FIG. 16A, a reflecting member 30 different from the electrode block 11 may be provided, and a part of a surface of the reflecting member 30 may form a reflecting surface 31. FIG. 16B is a perspective view schematically illustrating an example of the reflecting member 30. The reflecting member 30 includes an opening 32 in a part thereof, and the reflecting surface 31 is formed in a position on the −X side of the opening 32. By arranging the excimer lamp 3 in a position facing the opening 32 in the −X direction, the ultraviolet light L1 from the excimer lamp 3 is extracted to the outside through the opening 32. At that time, the ultraviolet light L1a having a relatively large divergence angle is reflected by the reflecting surface 31 of the reflecting member 30 to change the travel direction, so that the incident angle thereof when being incident on the optical filter 21 becomes smaller as is the case described above with reference to FIG. 12.

Figure 17:
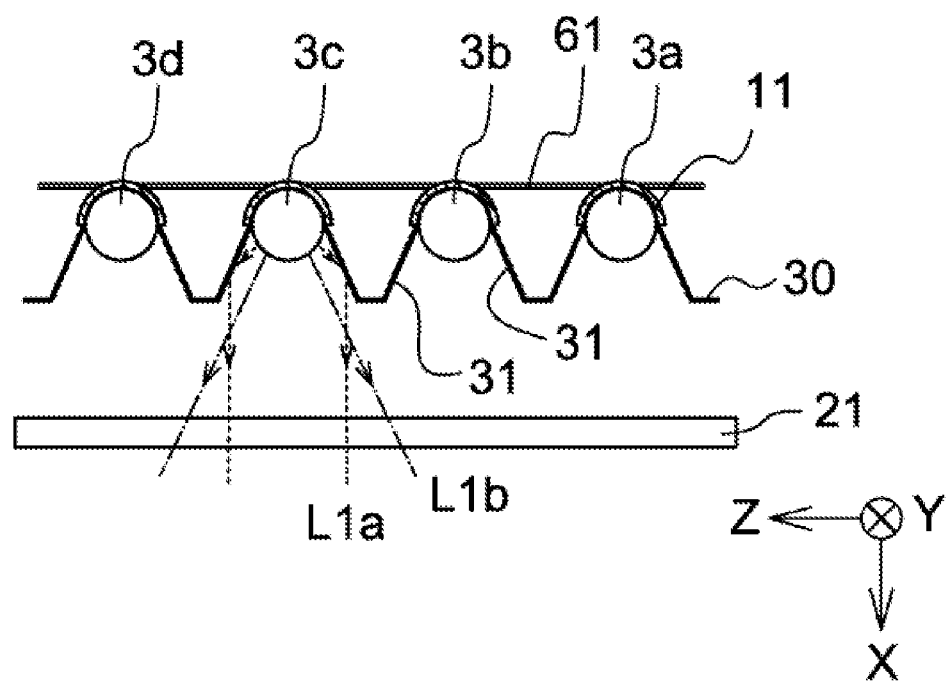
FIG. 17 is a view illustrating a schematic configuration of an ultraviolet irradiation device of another embodiment following FIG. 12.

Furthermore, in this case, each electrode does not have to have a block shape. That is, as illustrated in FIG. 17, the electrodes (11, 12) may be formed of a metal film formed by screen printing or the like on the outer side surface of the luminous tube of the excimer lamp 3. Note that, in FIG. 17, only the electrode 11 is illustrated for convenience of illustration. Note that, in order to electrically connect between the electrodes 11 and between the electrodes 12 provided on the outer side surface of the luminous tube of each of the excimer lamps (3a, 3b, 3c, 3d), the electrodes 11 and the electrodes 12 may each be connected to each other by the conductive member 61.

DESCRIPTION OF REFERENCE SIGNS

1 Ultraviolet irradiation device
2 Lamp house
2a Main body casing
2b Lid
3 Excimer lamp
3a, 3b, 3c, 3d Excimer lamp
3G Luminescent gas
10 Light extraction surface
11 First electrode block
11a Mounting area
11b Tapered surface
12 Second electrode block
12a Mounting area
12b Tapered surface
21 Optical filter
30 Reflecting member
31 Reflecting surface
32 Opening
61 Conductive member
111 Electrode block without tapered surface
L1 Ultraviolet light

The invention claimed is:

1. An ultraviolet irradiation device comprising:
a lamp house on at least one surface of which a light extraction surface is formed;
an excimer lamp accommodated in the lamp house in a position separated from the light extraction surface in a first direction, the excimer lamp that emits ultraviolet light, a main emission wavelength of which belongs to a first wavelength band of 190-225 nm;
a first electrode arranged in contact with an outer surface of a luminous tube of the excimer lamp;
a second electrode arranged in contact with the outer surface of the luminous tube of the excimer lamp in a position separated from the first electrode in a second direction parallel to a tube axis of the excimer lamp;
an optical filter that is arranged on the light extraction surface and substantially transmits the ultraviolet light in the first wavelength band and does not substantially transmit ultraviolet light of a wavelength of 240-300 nm; and
a reflecting surface that is a surface located outside the luminous tube of the excimer lamp and inclined with respect to the light extraction surface as seen in the second direction, the reflecting surface exhibiting reflectivity with respect to the ultraviolet light in the first wavelength band.

2. The ultraviolet irradiation device according to claim 1, wherein
the first electrode is a first electrode block in the shape of a block,
the second electrode is a second electrode block in the shape of a block, and
at least one of the first electrode and the second electrode includes a tapered surface forming the reflecting surface in a position away from the excimer lamp in a third direction orthogonal to the first direction and the second direction.

3. The ultraviolet irradiation device according to claim 2, comprising
the plurality of excimer lamps arranged so as to be separated from each other in the third direction, wherein
the first electrode block and the second electrode block are arranged so as to straddle the plurality of excimer lamps while being in contact with the outer surface of the luminous tube of each of the plurality of excimer lamps, and
the tapered surface is at least formed in a position interposed between the plurality of excimer lamps adjacent to each other in the third direction as seen in the second direction.

4. The ultraviolet irradiation device according to claim 2, wherein
a part of the tapered surface is located closer to the light extraction surface than the excimer lamp in the first direction.

5. The ultraviolet irradiation device according to claim 2, wherein
the tapered surface has an angle from the first direction of 10°-50° as seen in the second direction.

6. The ultraviolet irradiation device according to claim 2, wherein
both the first electrode block and the second electrode block have the tapered surface.

7. The ultraviolet irradiation device according to claim 2, wherein
the first electrode block and the second electrode block are made of Al, Al alloy, or stainless steel.

8. The ultraviolet irradiation device according to claim 1, wherein
a luminescent gas containing KrCl or KrBr is sealed in the excimer lamp.

9. The ultraviolet irradiation device according to claim 3, wherein
a part of the tapered surface is located closer to the light extraction surface than the excimer lamp in the first direction.

10. The ultraviolet irradiation device according to claim 3, wherein
the tapered surface has an angle from the first direction of 10°-50° as seen in the second direction.

11. The ultraviolet irradiation device according to claim 4, wherein
the tapered surface has an angle from the first direction of 10°-50° as seen in the second direction.

12. The ultraviolet irradiation device according to claim 9, wherein
the tapered surface has an angle from the first direction of 10°-50° as seen in the second direction.

13. The ultraviolet irradiation device according to claim 3, wherein
both the first electrode block and the second electrode block have the tapered surface.

14. The ultraviolet irradiation device according to claim 4, wherein
both the first electrode block and the second electrode block have the tapered surface.

15. The ultraviolet irradiation device according to claim 9, wherein
both the first electrode block and the second electrode block have the tapered surface.

16. The ultraviolet irradiation device according to claim 5, wherein
both the first electrode block and the second electrode block have the tapered surface.

17. The ultraviolet irradiation device according to claim 10, wherein
both the first electrode block and the second electrode block have the tapered surface.

18. The ultraviolet irradiation device according to claim 11, wherein
both the first electrode block and the second electrode block have the tapered surface.

19. The ultraviolet irradiation device according to claim 12, wherein
both the first electrode block and the second electrode block have the tapered surface.

* * * * *